(12) United States Patent
Weijers et al.

(10) Patent No.: US 8,086,000 B2
(45) Date of Patent: Dec. 27, 2011

(54) METHOD, APPARATUS AND COMPUTER PROGRAM FOR QUANTITATIVE BIFURCATION ANALYSIS ON ANGIOGRAPHIC IMAGES

(75) Inventors: Bas Weijers, Maasmechelen (BE); Jean-Paul Michel Maria Aben, Limbricht (NL); Christian Consten, Maastricht (NL); Jacobus Adrianus Engelbertus Johannes Hof, La Kerkrade (NL)

(73) Assignee: Pie Medical Imaging B.V., Maastricht (NL)

(*) Notice: Subject to any disclaimer, the term of this patent is extended or adjusted under 35 U.S.C. 154(b) by 966 days.

(21) Appl. No.: 11/845,154

(22) Filed: Aug. 27, 2007

(65) Prior Publication Data
US 2009/0060298 A1 Mar. 5, 2009

(51) Int. Cl.
*G06K 9/00* (2006.01)
(52) U.S. Cl. ......... 382/128; 382/130; 382/131; 600/407
(58) Field of Classification Search .......... 382/128, 382/130, 131; 600/407
See application file for complete search history.

(56) References Cited

U.S. PATENT DOCUMENTS

2004/0120561 A1* 6/2004 Goto ............................. 382/128
2006/0062447 A1* 3/2006 Rinck et al. .................. 382/154

OTHER PUBLICATIONS

A New Quantitative Analysis System for the Evaluation of Coronary Bifurcation Lesions: Comparison with Current Conventional Methods, Omer Goktekin, MD et al., Catheterization and Cardiovascular Interventions 69: pp. 172-180 (2007).
CAAS II: A Second Generation System for Off-Line and On-Line Quantitative Coronary Angiography, Ed Gronenschile, PHD et al. Catheterization and Cardiovascular Diagnosis 33: pp. 61-75 (1994).
Introduction to Algorithms, Thomas H. Cormen et al., The MIT Press, Twentieth Printing, 1998, pp. 527-532.

* cited by examiner

*Primary Examiner* — Vikkram Bali
*Assistant Examiner* — Katrina Fujita
(74) *Attorney, Agent, or Firm* — Gordon & Jacobson, PC

(57) ABSTRACT

A method, data processing facility and program storage device for quantitative analysis on medical image data of a bifurcated tubular organ which involves processing the medical image data to identify contours of the bifurcated tubular organ. The contours are used to determine a Polygon of Confluence amongst the bifurcated tubular organ. The Polygon of Confluence is used to determine at least one parameter value characterizing geometry of the bifurcated tubular organ. The at least one parameter value is outputted to a user for angiography purposes. The at least one parameter value can include at least one diameter value of the bifurcated tubular organ, at least one angle value between parts of the bifurcated tubular organ, and at least one reference diameter value for the bifurcated tubular organ, the at least one reference diameter value compensating for damage to the bifurcated tubular organ.

25 Claims, 8 Drawing Sheets

11a

11b

METHOD, APPARATUS AND COMPUTER PROGRAM FOR QUANTITATIVE BIFURCATION ANALYSIS ON ANGIOGRAPHIC IMAGES

BACKGROUND OF THE INVENTION

1. Field of the Invention

The present invention relates to a method for quantitative bifurcation analysis of medical images, in particular angiographic images.

2. State of the Art

Angiography, in particular coronary angiography, refers to the process of investigating coronary arteries to determine the severity of any narrowing that may exist, such as by finding stenotic arteries. Quantitative Coronary Analysis (QCA) of single vessels has become a standard for guiding interventions and executing trail studies in coronary revascularization. However, angiographic analysis of lesions in or near a bifurcation presents a considerable problem since QCA for single vessels cannot handle more complex geometries. The definition of bifurcation herein is a splitting of a main tubular vessel into two or more further tubular vessels. For example, the left coronary artery bifurcates into the left anterior descending artery and the left circumflex artery.

QCA of a bifurcation involves automatic segmentation of the bifurcation. This can be followed by reconstructing a healthy state that includes the bifurcation area itself. The reference vessel diameter, which means the vessel's healthy diameter as computed by the QCA, is typically based on averages of the vessel "normal" parts before and after the bifurcation, respectively. So the greatest challenge for bifurcation lesion analysis is extracting the true reference vessel size of both the proximal vessel and its side branches. Conventional QCA detects vessel contours assuming minimal vessel tapering and cannot handle large steps in diameter caused by the bifurcation itself.

Most conventional QCA methods allow inputting a user-defined reference, which could eliminate the wrong reference definition. However this reference diameter would still only be valid on the one side of the bifurcation where the user defined the reference. This option is furthermore little reproducible such as through operator inaccuracy and subjectivity.

Currently no detailed publication has solved the above limitations. O. Goktekin et al, "A new quantitative analysis system for the evaluation of coronary bifurcation lesions: Comparison with current conventional methods", Catheterization and Cardiovascular Interventions 69:172-180 (2007), evaluates a bifurcation package, in which the bifurcation is divided into three parts on each of which conventional QCA is applied. Goktekin describes a method for solving the reference problem by eliminating the central bifurcation area from the reference calculations. Therefore, the central bifurcation is still left out of consideration, both for calculating a diameter, and also for definition of a reference.

SUMMARY OF THE INVENTION

It is therefore an object of the invention to provide a more accurate and reproducible method and system for executing quantitative analysis of a bifurcation to solve the limitations in prior art. The object is realized according to the invention by methodology for quantitative analysis on medical image data of a bifurcated tubular organ. The methodology involves processing the medical image data to identify contours of the bifurcated tubular organ. The contours are used to determine a Polygon of Confluence amongst the bifurcated tubular organ. The Polygon of Confluence is used to determine at least one parameter value characterizing geometry of the bifurcated tubular organ. The at least one parameter value is outputted to a user for angiography purposes. The at least one parameter value can include at least one diameter value of the bifurcated tubular organ, at least one angle value between parts of the bifurcated tubular organ, and at least one reference diameter value for the bifurcated tubular organ, the at least one reference diameter value compensating for damage to the bifurcated tubular organ.

The methodology of the present invention has been found to yield stable and correct results for many complex situations at a cost of relatively straightforward operations. An important advantage of determining an angle or a diameter in accordance with the methodology of the present invention is that these results form an improved tool for a surgeon to select in practice a suitable surgical part or device such as a stent or a dottering element.

The invention relates also to a data processing facility and to a program storage device for carrying out the methodology of the present invention.

Various advantageous aspects of the present invention are recited in dependent claims.

Moreover, although the foregoing generally recites coronary arteries, the principle of the invention is also applicable to other arteries, to veins, and in general to various tubular organs that may benefit from their angiographic imaging being assisted through the present invention's improvements. In consequence, the term artery should in the context of the present invention be considered as having a broader meaning.

Additional objects and advantages of the invention will become apparent to those skilled in the art upon reference to the detailed description taken in conjunction with the provided figures.

BRIEF DESCRIPTION OF THE DRAWINGS

Now, the invention will hereinafter be discussed more in detail with reference to the detailed disclosure hereinafter of the preferred embodiment, and more in particular with reference to the Figures that illustrate.

DETAILED DESCRIPTION OF THE PREFERRED EMBODIMENT

Figure 1:
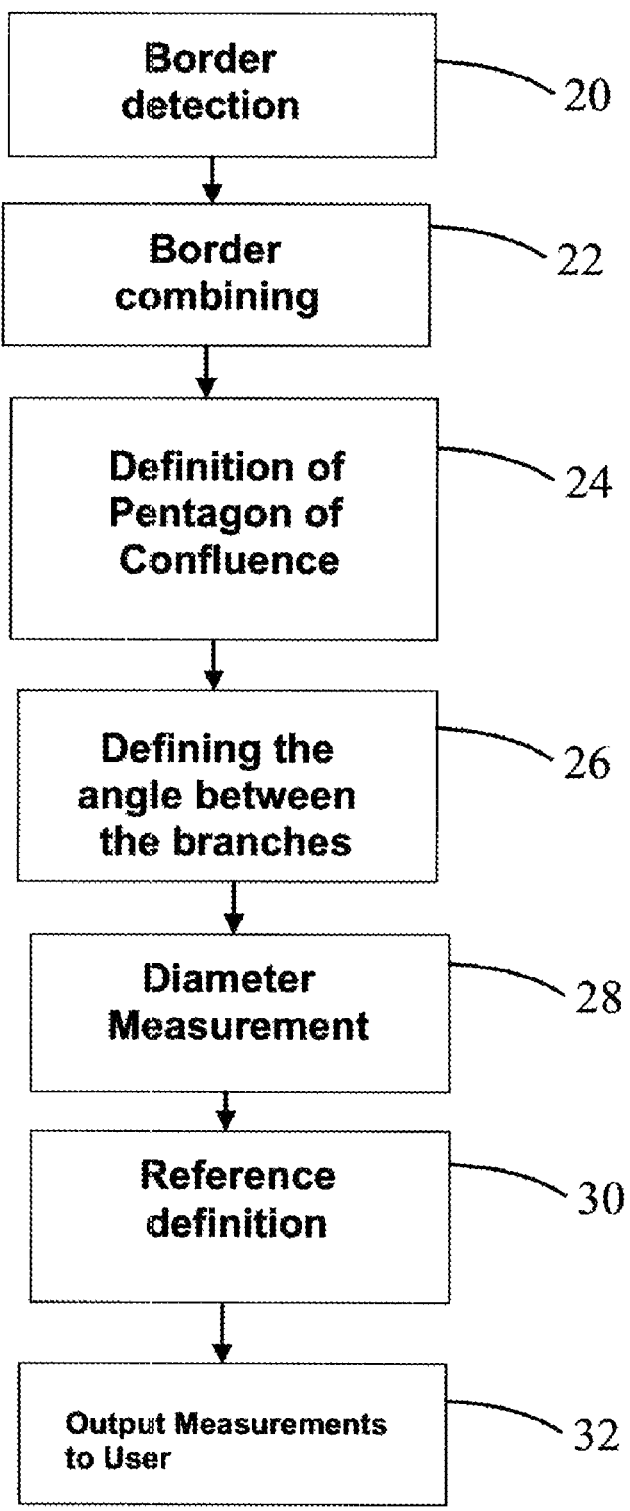
FIG. 1 is a flow diagram of processing the bifurcation data.

FIG. 1 illustrates a flow diagram for processing the bifurcation data. Therein, block 20 represents the border detection, block 22 the border combining, block 24 the defining of a Pentagon of Confluence, block 26 the defining of the angles between the branches, block 28 the diameter measurement, block 30 the reference definition and block 32 the measurements of block 26, 28 and 30 are output to the user, for example as part of a display screen or printout. Hereinafter, each one of blocks 20-28 as defined in the diagram is described in detail. The methodology of the present invention is preferably carried out by a data processing facility such as computer workstation that includes a data processing platform (e.g., CPU, memory system, non-volatile storage, display adapter) that interfaces to user input devices (such as a keyboard and pointing device) and one or more display devices and/or printer for user output. The methodology of the present invention is preferably realized as a software application that is stored on one or more optical discs (or other form of non-volatile memory), or possibly downloaded from a remote computer system, and loaded onto the data processing platform for execution thereon.

Figure 2:
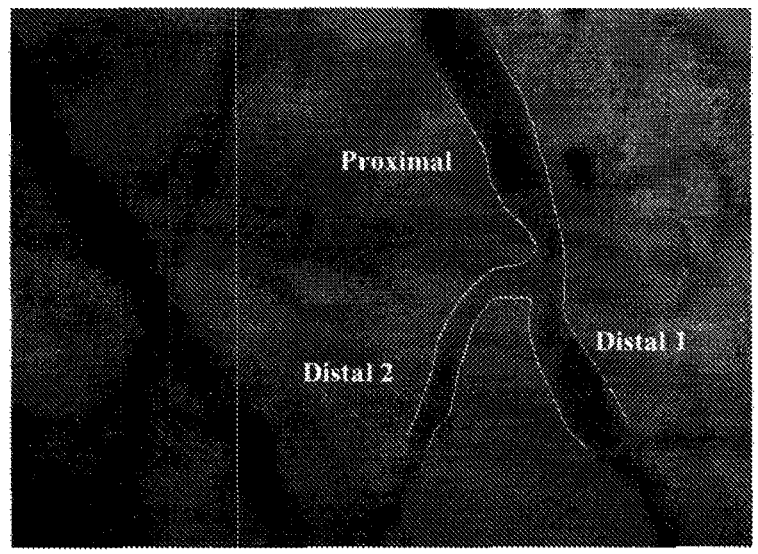
FIG. 2 is an example of a bifurcation angiographic image.

FIG. 2 illustrates a typical example of a bifurcation, or more generally, a tubular organ in an angiographic image. For a quantitative bifurcation analysis, the vessels "connecting" to the bifurcation have to be detected. Here, the three vessels are the proximal vessel, the first distal (i.e. the distal part of the main branch) and second distal (i.e. the distal part of the side branch) vessel. The two distal vessels may be or may not be of equal size, and the steps executed for visually showing the bifurcation image in an optimum manner are considered state of the art. Instead of attempting to depict the bifurcation as two or three vessels that share common parts, the bifurcated vessel is seen as one object delineated by a left, a middle and a right highlighted contour without further assumptions.

The detection of the bifurcation can start in either of three different ways (cf. block 20).

The first method to start the detection of the bifurcation is that the user roughly indicates the arterial bifurcation center line in a number of points in such a way that all the lines connecting the points are roughly within the main branch (proximal and distal 1) and side branch (distal 2 from the center of the bifurcation). An example of this approach is given in Gronenschild and Tijdens, "A second Generation System for Off-line and On-line Quantitative Coronary Angiography", Catheterization and Cardiovascular Diagnosis 33:61-75 (1994).

The second method to start the detection of the bifurcation is by letting the user indicates a start point in the proximal branch and end points in each of distal 1 and distal 2. From these points the three path lines are automatically computed by using a wave front algorithm. Such algorithm simulates wave front propagation such as a water wave through a river. See Introduction to Algorithms, Thomas H. Cormen, Charles E. Leiserson, Ronald L. Rivest, ©1990 The MIT Press Cambridge, Mass. London, England. Chapter 25.2, Dijkstra's algorithm, page 527-532.

Figure 3:
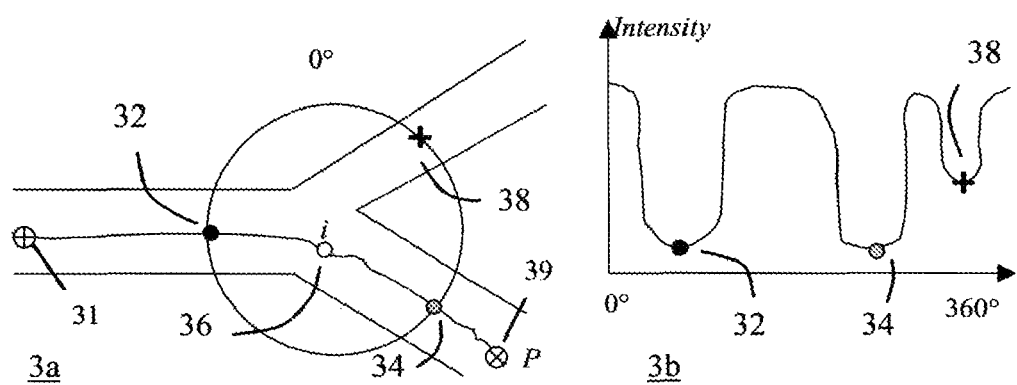
FIGS. 3a and 3b are diagrams illustrating a path-line extending from a corrected user point.

The third method to start the detection of the bifurcation is by letting the user indicate the center of the bifurcation, which starts an automatic path line extraction in the three branches. The method is again based on the wave front algorithm. Considering that the major drawback in current systems for analyzing bifurcation lesions is the absence of a reliable reference definition, our preferred method automatically stops the propagation of the path line either when a branch is detected or when a predefined length is reached, such as at points 31, 39 in FIG. 3a. This will stabilize the definition of a reference in each branch and mitigate user variability and generates a highly reproducible definition of the vessel segment(s) of interest. FIGS. 3a, b illustrates a path-line extending from a corrected user point and its image density for finding the path lines for the three branches (proximal, distal1 and distal2). In order to restrict the propagation (as long as its predefined length is not reach), the wave front propagation is extended with a junction/branch detection. First, at point i (36) we look at the density profile along the circle with center i and radius n times r where r is the vessel radius at point i, and n is a suitable factor greater than one, such as lying between 1,5 and 5. If i is indeed a junction point, the density profile will have three dips (such as points 32, 34, 38 in FIG. 3b) corresponding to the three vessels at the junction. Each dip has a width that relates to the local width of the vessel. Two of the dips (32, 34) can already be linked to a vessel because the path-line through point P passes through two of the vessels connected at the junction. Let's call the index values along the circle of the points of intersection with the path line i1 and i2 (the black and gray dots 32, 34 in both FIGS. 3a, 3b). We also know the widths of these two dips because the radius of the two vessels is known from the adapted wave front algorithm for every point along the path line.

Figure 4:
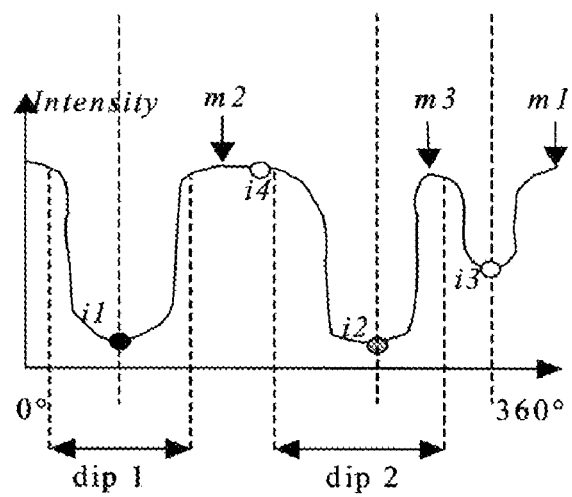
FIG. 4 is a diagram illustrating various maxima within regions bounded as shown.

FIG. 4 illustrates the amplitudes in regions bounded as shown. First, dip 1 and dip 2 have been indicated as horizontal arrows that project as dashed lines on the intensity profile. Outside the dips at 32, 34, two index ranges lie along the circle. In either range the index with lowest intensity has been indicated as i3, i4, respectively.

We now consider the sets of indexes {i1,i2,i3} and {i1,i2,i4} separately. We want to know whether i3 or i4 (or both) is the center of a vessel that has a dip size comparable to i1 and i2. First, consider {i1,i2,i3}. The algorithm for the second set is the same. We look for the intensity maxima m1, m2, m3 in the ranges bounded by {i1,i2,i3}. These maxima define the left and right background intensity of the vessels. From this we define minimum background intensities bmin1, bmin2, bmin3 and maximum background intensities bmax1, bmax2, bmax3 of the three vessels.

Note that in FIGS. 3b and 4, the profile on the 360° circle has no real end: that's why m1 is located at the end of the curve. From the figure, it holds that bmin1=MIN(m1, m2), bmin2=MIN(m2, m3), bmin3=MIN(m3, m1), and bmax1=MAX(m1, m2), bmax2=MAX (m2, m3), bmax3=MAX (m3, m1). The procedure may vary somewhat, for example if i2 were located before i1. The minimum contrast can then be defined for the vessels as:

cmin1=bmin1-intensity at i1
cmin2=bmin2-intensity at i2
cmin3=bmin3-intensity at i3

The maximum contrast can then be defined for the vessels as:

cmax1=bmax1-intensity at i1
cmax2=bmax2-intensity at i2
cmax3=bmax3-intensity at i3

We assume that i3 is a point inside the third vessel if the following conditions hold:

cmin1, cmin2, cmin3 all are above a threshold (n) the image noise level.

cmax3 has a contrast at least equal to n1*MIN(cmax1, cmax2), where n1 is a threshold. This allows ignoring weak background structures and irrelevant details, such as a much smaller vessel separating from the main vessel.

If the contrast at left and right from the vessels differs, the contrast of the vessel with the background is higher than if the contrast at the left and right vessel is the same but lower than in the first case. In order to take this into account we define the enhanced contrast of the three vessels by multiplying the minimum contrast value by 1.5 while ensuring that the result is at most the maximum contrast value:

enh1=MAX(cmax1, n2*cmin1)
enh2=MAX(cmax2, n2*cmin2)
enh3=MAX(cmax3, n2*cmin3)

Now it must hold that enh3 is larger than 0.4*MAX(enh2, enh3). So the enhanced contrast of the third vessel must be at least about half the maximum of the enhanced contrasts of the other two vessels. Now if i3 (or i4) is the third vessel then there are 3 vessels at point i and i (36) is assumed to be a junction point.

The above methodology to find the path from one position can be applied to a single vessel. In that case, the path line will terminate either at a proximal/distal bifurcation or otherwise at a predetermined distance from the indicated user point.

The above methodology can be extended to multiple bifurcations, such as a vessel tree. It should then be adapted to proceed at the first proximal or distal bifurcation whilst defining another limiting number. The stopping distance can be maintained.

The above methodology can be expanded to preprocessing the position of the user-indicated point for correcting a possible misplacement, which results in an even higher reproducibility. This could even allow for a start location outside the vessel.

The preprocessing generates four bidirectional scan lines with predefined lengths that cross the user point in horizontal, vertical and diagonal directions. Using a multi-scale approach the vessel centers are sought on the scan lines. A combination of the first derivative and the negated second discrete derivative of the density along each scan line is computed on a set of different scales. This is done by convolving the scan lines with the negated first and negated second derivatives of the one-dimensional Gaussian function. A point c on scan line k is the center of a vessel that has diameter z if and only if:

There is a zero-crossing in the negation of the first derivative of the scan line k on scale s=ceil(z/2)

Figure 5:
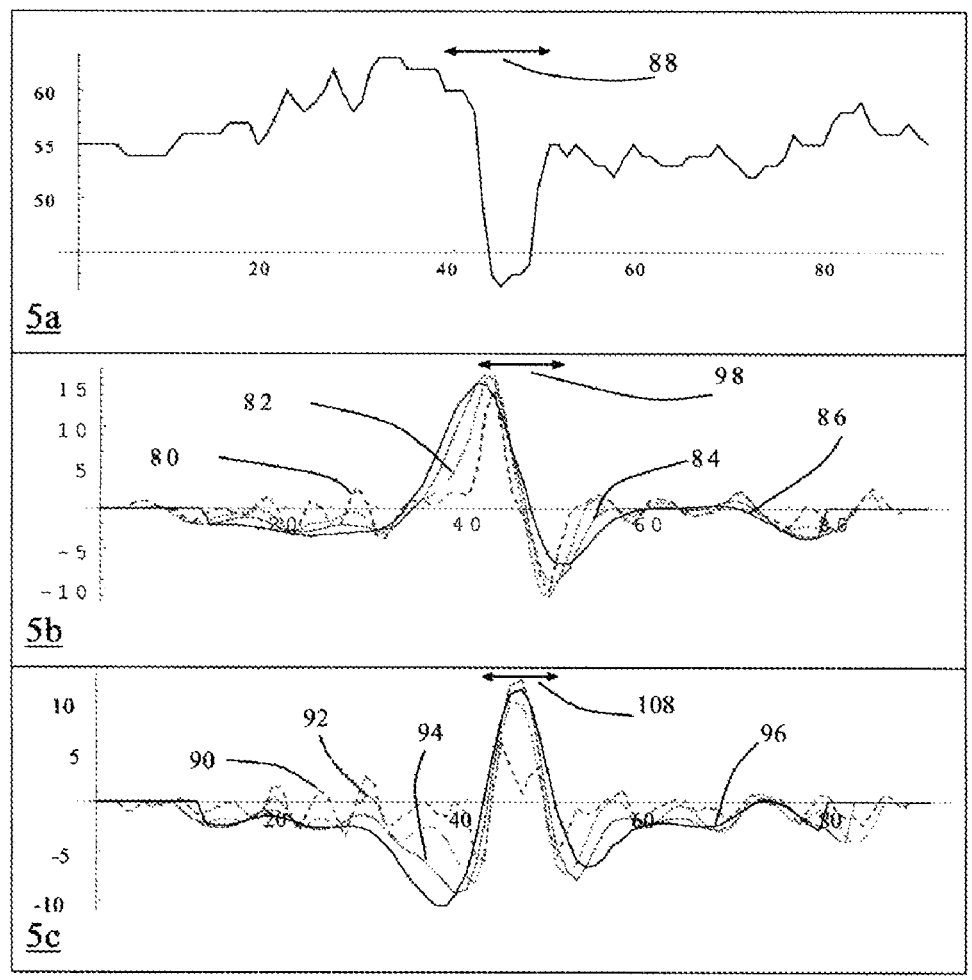
FIGS. 5a, 5b and 5c are diagrams illustrating multi-scale responses of an intensity profile.

The negation of the second derivative at c on scale s is a positive value and is maximal over all indexes j with a zero-crossing on any scale in S with j∈[c−z, c+z] on scan line k As an example, FIGS. 5*a* to 5*c* illustrate multi-scale responses of the intensity profile along a scan line. FIG. 5*a* has the unprocessed profile, wherein the horizontal scale is in pixels along the scan line. FIG. 5*b* shows the negated Gaussian first derivative scale space of the intensity profile at scale parameter values 1, 2, 3 and 4, respectively (80, 82, 84, 86). At the vessel center (roughly at horizontal index 46), we see a zero crossing in the first derivative at all scales. Likewise, FIG. 5*c* shows the negated Gaussian second derivative scale space of the intensity profile at scale parameter values 1, 2, 3 and 4, respectively (90, 92, 94, 96). Here, there is a maximum in scale 3 (94), which corresponds to a vessel diameter of 6 (in units of the horizontal axis). No higher negated second order derivatives have zero crossings within this diameter at either side from the maximum. This range has been indicated by arrows 88, 98. See also 108. This shows the detecting of a vessel at index 46 with a diameter 6 (scale values arbitrary in principle). This concludes our example.

Now, if the Euclidian distance from the above-defined c to the user point is at most z, where z is the vessel diameter at c, all other candidate center points are discarded. We now determine the maximum negated second derivative D among the un-discarded candidates.

At last, we move the user point to the candidate vessel center that is closest to the user point among all candidates with a negated second derivative of at least 0.5*D. The check on the second derivative prevents the user point from being moved to a background structure: due to the presence of contrast fluid, the second derivative at a vessel center will be much higher than that of a background structure.

We now have three path lines and the detection of the bifurcation can be reduced to three conventional edge detections, for example by using the minimum cost algorithm described by the Gronenschild and Tijdens reference, of record.

Now, the centerlines should effectively join at the "Point of Bifurcation". Each centerline results from the algorithm used for the edge detection. In summary it's the middle between the detected contours on each location along the vessel.

As an initial guess for the "Point of Bifurcation", the last point on the centerline of the proximal vessel is used. First, closest points on the bifurcation boundaries are located: $\overline{b}_{left,i}$, $\overline{b}_{right,j}, \overline{b}_{mid,k}$. Through these points, a circle is fitted and the midpoint of this circle is used as a better approximation for the point of bifurcation. This is applied iteratively until the point of bifurcation does not change significantly anymore:

1. PoB=$\overline{c}_0$
2. Find the contour points on the left ($\overline{b}_{left,i}$), right ($\overline{b}_{right,j}$) and middle ($\overline{b}_{mid,k}$) boundary closest to $\overline{c}_t$
3. Fit a circle through these points: $<\overline{b}_{left,i},\overline{b}_{right,j},\overline{b}_{mid,k}> \rightarrow (\overline{c}_{t+1}, r)$
4. PoB=$\overline{c}_{t+1}$
5. If $|\overline{c}_{t+1}-\overline{c}_t|<\epsilon \Rightarrow$ Quit
6. t+1→ go to step 2

At the end of these iterations, the Point of Bifurcation is equal to the midpoint of the biggest circle that fits inside the bifurcation.

Figure 6:
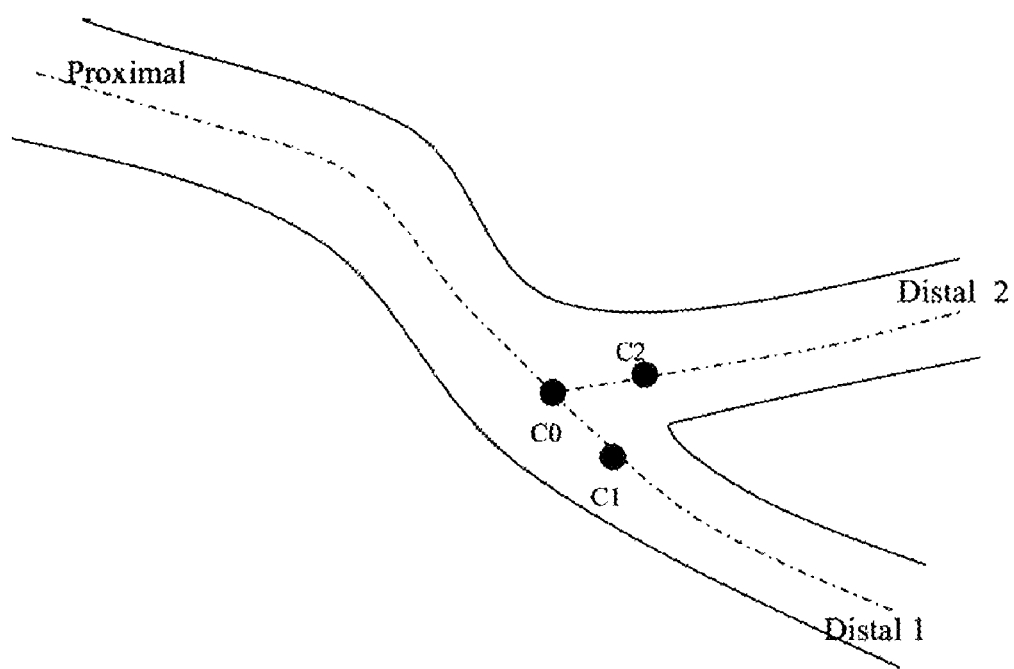
FIG. 6 is a diagram illustrating points used to determine the left and right vessels.
Figure 7:
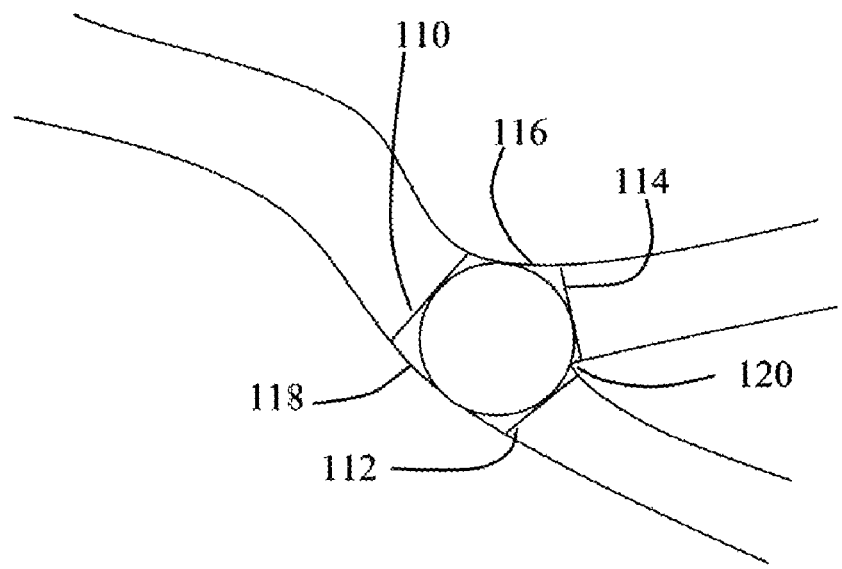
FIG. 7 illustrates an exemplary pentagon of confluence in accordance with the present invention.

Now, we will describe the border combining (block 22 in FIG. 1). The contours around the three vessels produced by a method such as described in the Gronenschild and Tijdens reference, of record, must now be combined. In this respect, FIG. 6 illustrates the three points c0, c1, c2 that are used to determine the left and right vessels. FIG. 7 illustrates an exemplary Pentagon of Confluence.

In FIG. 6, the points c0, c 1, c2 are the Point of Bifurcation and arbitrary centerline points close to the Pentagon of Confluence on the first distal vessel and the second distal vessel, respectively. The orientation is given by the sinus of the angle $c_1 c_0 c_2$. If positive, then $c_2$ lies left of $c_1$. Otherwise, $C_2$ lies right of $c_1$:

$$(c_1 - c_0) \cdot \begin{pmatrix} 0 & 1 \\ 1 & 0 \end{pmatrix} (c_2 - c_0) > 0 \Rightarrow c_2 \text{ left of } c_1, \quad (1)$$

distal 1 is the right vessel $$< 0 \Rightarrow c_2 \text{ right of } c_1,$$

distal 2 is the right vessel

After determining the orientation of the bifurcation, we know which contours to combine:

The left contour of the proximal vessel needs to be combined with the left contour of the left distal vessel The right contour of the proximal vessel needs to be combined with the right contour of the right distal vessel The left contour of the right distal vessel is swapped and combined with the right contour of the left distal vessel. The swapping is needed since the contours need to go in the same direction.

The combining itself is done by checking if the two contours cross each other or are close together. For each point along one contour (designated by $\overline{b}_{1,n}$), the vector to three subsequent points on the other contour (designated by $\overline{b}_{2,m+\{-1,0,1\}}$) is calculated and the inner product is used to determine if the vectors point in the same direction. If this is not the case the contour crossed the other contour:

$$\overline{v}_i = \overline{b}_{2,m+i} - \overline{b}_{1,n} (i \in \{-1,0,1\})$$

$$\overline{v}_{-1} \cdot \overline{v}_1 < 0 \Leftrightarrow \text{crossing} \qquad (2)$$

Furthermore, when at a certain point the two boundaries are closer together than a certain amount of pixels, they are also seen as combinable:

$$|v_0| < n \text{ pixels} \vee \text{crossing} \Rightarrow MERGE \qquad (3)$$

The results of the bifurcation segmentation are three edges illustrated in FIG. 2. Block 24 in FIG. 1 represents the definition of the "Pentagon of Confluence". For determining the end of the bifurcation- and the start of bifurcation region, we first construct the largest circle that fits inside the bifurcation. The intersections of this circle with the centerlines are the positions that represent the bifurcation region. The point in the proximal part represents the Start of Bifurcation and the points in the distal parts represent the Ends of Bifurcation; this area is called the "Pentagon of Confluence". Three edges of the pentagon 110, 112, 114 each lie across one of the channels. Two edges of the pentagon 116, 118 lie along the outer sides of the channels. Where the two edges 112, 114 meet at 120, only a small space is present that is approximated by a vertex of the pentagon. In rare cases, a hexagon could better fit to the measured points.

Figure 8:
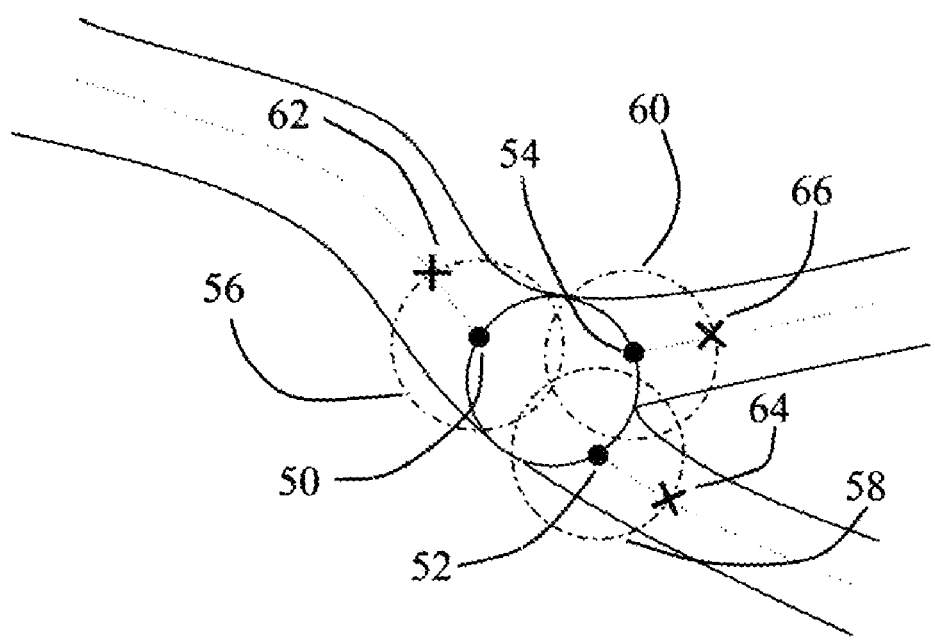
FIG. 8 illustrates the calculation of the angles between the various branches of a bifurcation in accordance with the methodology of the present invention.

Block 26 in FIG. 1 shows how the angles between the branches are calculated. FIG. 8 illustrates the calculation of the angles between the various branches; the dots and crosses are the intersection points for determining the edges of the pentagon. The angles between the arterial branches connecting to the pentagon of confluence are calculated according to the following highly reproducible method. The influence of the position of the center of bifurcation (Point of Bifurcation) is eliminated in this manner. Within each branch a part of the vessel is defined near the Pentagon of Confluence that represents the direction of that particular branch. This direction is indicated by a line piece based on the centerline of that branch.

For the starting point of these line pieces, we use the circle from the definition of the "Pentagon of Confluence". The intersection positions (50, 52, 54 in FIG. 8) of the circle with the centerlines are the start positions of the line pieces. Then we use each of these intersection points as the center of a new circle (56, 58, 60, respectively). These new circles have the same radius as the circle that is located within the "Pentagon of Confluence" or a radius that depends on the mean vessel diameter of the specific branch. The intersections of these new circles with the centerlines are the end points of the line pieces (62, 64, 66, respectively). The latter intersection points are the start and end points of the line pieces for use in the angle determination. We now construct three line pieces between the intersection points. For each of these lines we can calculate the tangent and thus the angle. The diameter along the bifurcation is measured according to block 28 in FIG. 1. The arrangement of a bifurcation consists of left, middle and right borders. The diameter measurement within the Pentagon of Confluence is based on the "Minimum Freedom" approach. This approach is performed on each point walking from the borders of the Pentagon of Confluence towards the center point within the Pentagon of Confluence. Each scan point is centered within the borders.

For each scan point $\overline{c}_i$; the "Minimum Freedom" approach is performed, as follows:
1. Find the border points on the left ($\overline{b}_{left,i}$), right ($\overline{b}_{right,j}$) and middle ($\overline{b}_{mid,k}$) boundary closest to $\overline{c}_i$
2. calculate the distances between the three points: $\{\overline{b}_{left,i}, \overline{b}_{right,j}, \overline{b}_{mid,k}\} \rightarrow \{d_{lr}, d_{lm}, d_{rm}\}$
3. if vessel=proximal $\Rightarrow$  $d_i = d_{lr}$
   if vessel=left distal $\Rightarrow$ $d_i = \min(d_{lr}, d_{lm})$
   if vessel=right distal $\Rightarrow$ $d_i = \min(d_{lr}, d_{rm})$

| Formula legend | |
|---|---|
| left | On position of the left border |
| right | On position of the right border |
| mid | On position of the middle border |
| lr | From the left border to the right border point closest to the scan point |
| lm | From the left border to the middle border point closest to the scan point |
| rm | From the right border to the middle border point closest to the scan point |
| b | Closest point on border |
| d | Distance |

Figure 9:
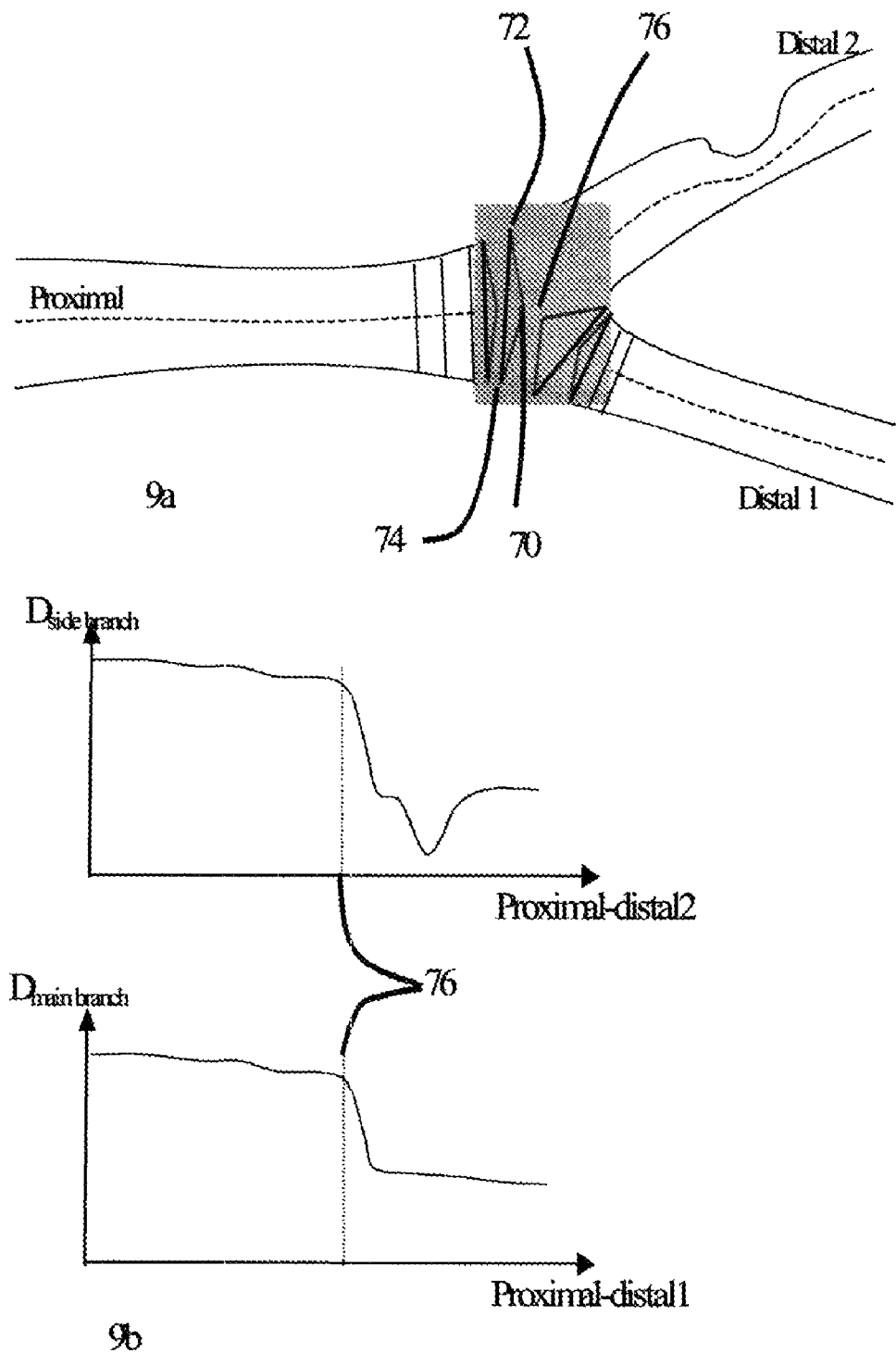
FIGS. 9a and 9b are diagrams that illustrate the calculation of the diameter of a bifurcation in accordance with the methodology of the present invention.

FIG. 9 explains visually the calculation of the bifurcation diameter through introducing the above new metric. Within the pentagon of confluence, indicated by the shaded part in FIG. 9a, one diameter at an arbitrary centerline position 70 within the pentagon of confluence is calculated as the distances between the border points 72 and 74 which are located by searching for the border position having the shortest distance to the centerline point 70. Note that the diameter D, as shown in FIG. 9b, from proximal till the point of bifurcation 76 of the main branch and the side branch are identical, since the centerline splits up at the point of bifurcation 76 into distal1 and distal2. Diameters outside the pentagon of confluence are determined as the distance between left and right borders of the specific branch as described in the Gronenschild and Tijdens reference, of record.

Block 30 in FIG. 1 represents the reference definition along the bifurcation. Acquired lesions can be expressed by quantities such as percentage narrowing, and therefore, a healthy vessel is reconstructed by defining its diameter. Prior art is limited in defining the true "reference" that compensates for acquired lesions for both the proximal vessel and its side branches as well as within the Pentagon of Confluence. Especially, reconstructing the Pentagon of Confluence is a challenging task.

Now first, for each branch a reference quantity is calculated such as disclosed in the Gronenschild and Tijdens prior art, of record. Based on the reconstructed edges derived from these quantities, the reference quantity inside the pentagon of confluence is interpolated my means of a novel curvature-based interpolation technique described below.

First, a few assumptions allow to reconstruct the edges of the "Pentagon of Confluence". Therefrom, the reconstruction method follows logically.

Figure 10:
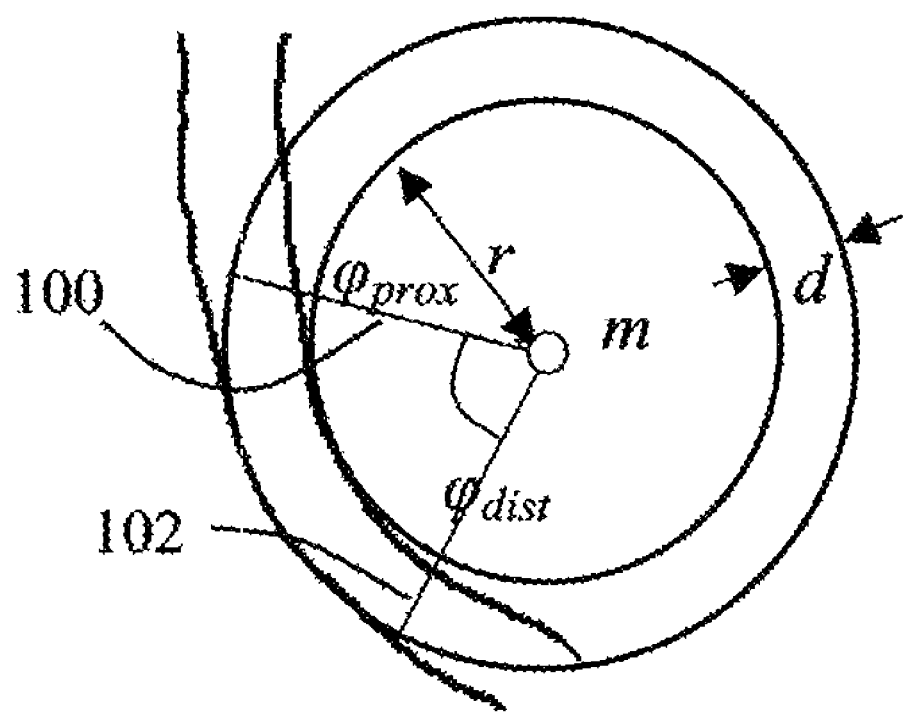
FIG. 10 is a diagram illustrating the modeling of part of a vessel through an annulus.

Assumptions (bifurcation)
  B1. The blood flows smoothly from the proximal vessel to the two distal vessels
  B2. At the "Pentagon of Confluence", the curvature is constant The equivalent assumptions for a single vessel are as follows:
  V1. The blood flows smoothly through a healthy vessel
  V2. Locally, the curvature of a healthy vessel is constant Assumption V1 implies that the diameter of a vessel does not change much. Since we look only at a local model, this is true for healthy vessel. Assumption V2 implies that we can use a model of constant curvature, the associated curve being a circle. Extending this idea to an object with constant diameter produces a torus in 3D and an annulus in 2D. In 2D a vessel can therefore be modeled locally as part of an annulus, as illustrated in FIG. 10. The annulus is described by its inner radius (r; reciprocal to the curvature), its width (d; equal to the width of the vessel) and by a segment for which the local model holds between indicated angles $\phi_{prox}$ (100) and $\phi_{dist}$ (102).

This leads to the following model:

$$\langle m, r, d \rangle \rightarrow \begin{cases} \overline{b}_{left} = \overline{m} + r\begin{pmatrix} \sin\varphi \\ \cos\varphi \end{pmatrix} \\ \overline{b}_{right} = \overline{m} + (r+d)\begin{pmatrix} \sin\varphi \\ \cos\varphi \end{pmatrix} \end{cases} ; \varphi \in \varphi_{prox} : \varphi_{dist} \quad (4)$$

The orientation of the vessel can be modeled by changing the sign of d. When d is negative, the right contour will be the shortest, giving a vessel that turns to the right:

$$\begin{cases} d > 0 \Leftrightarrow \text{vessel turns left} \\ d < 0 \Leftrightarrow \text{vessel turns right} \end{cases} \quad (5)$$

However, the absolute value of d is still equal to the diameter of the vessel.

To meet assumptions B1 and B2, the model is extended to a bifurcation. For a bifurcation, we have three widths: $d_{prox}$, $d_{left}$, and $d_{right}$. Due to assumption B2, the curvature should not change when moving from proximal to one of the distal vessels. Hence, the three widths have to be combined with two inner radii: $r_{left}$ and $r_{right}$, that gives three annuli.

The first two annuli guarantee assumption B1 for the left branch. The last two annuli guarantee assumption B1 for the right branch. The first two have the left boundary in common, whereas the last two have the right boundary in common:

$$\overline{b}_{left} = \overline{m}_{left} + r_{left}\begin{pmatrix} \sin\varphi \\ \cos\varphi \end{pmatrix}$$

$$\overline{b}_{right} = \overline{m}_{right} + r_{right}\begin{pmatrix} \sin\varphi \\ \cos\varphi \end{pmatrix} \quad (6)$$

The boundaries are found by fitting the set of four annuli to some reference points in the bifurcation. Let us have two proximal points 130, 132, two left distal points 134, 136, and two right distal points 138, 140.

Figure 11:
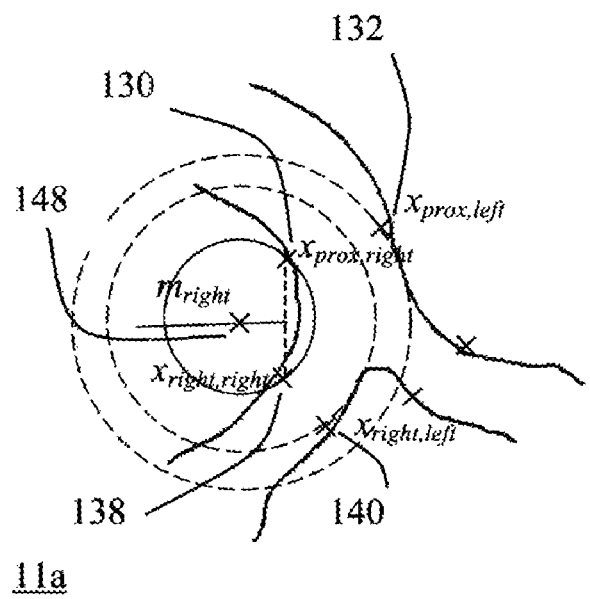
FIGS. 11a and 11b are diagrams illustrating the modeling of a bifurcation by a set of annuli.
Figure 11:
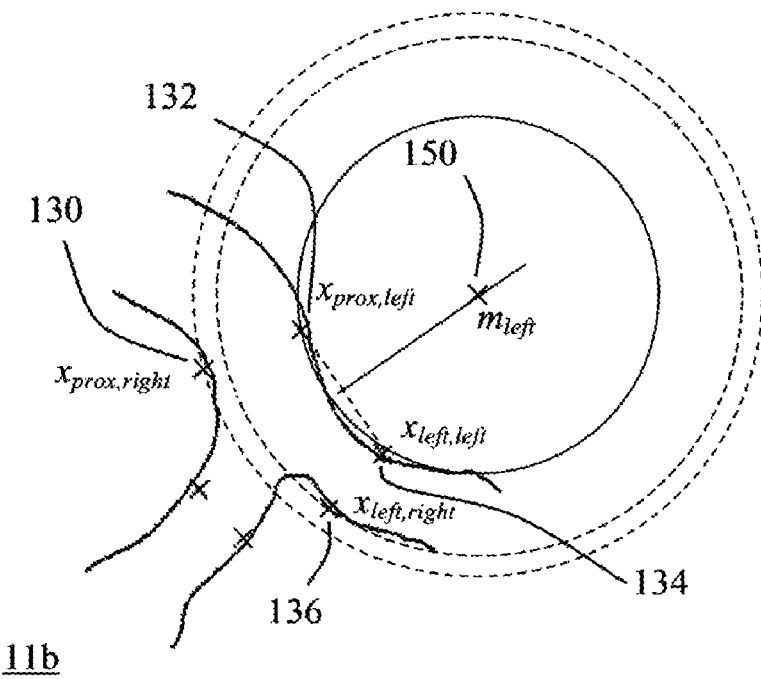

FIGS. 11a, 11b illustrate the modeling of a bifurcation by a set of annuli. For the right border (FIG. 11a), the midpoints of two annuli are located somewhere on the line perpendicular to the two right points 130 and 138 ($\phi_{prox, right}$ and $\phi_{right,right}$).

The position on the line is determined by fitting the "proximal, left" point 132 to the $\langle \overline{m}_{right}, r_{right}, d_{prox} \rangle$ annulus and the "right,left" point 140 to the $\langle \overline{m}_{right}, r_{right}, d_{right} \rangle$ annulus. The equivalent is done for the left border as shown in FIG. 11b (right image). The midpoints of the annuli are indicated as 148, 150, respectively.

For each of the right and left borders, four of the six points are used to fit the annuli.

In general, four points and two widths are used to find the parameters of two annuli, that is done as follows:

1. Define a line of possible midpoints:

$$\overline{m}(\lambda) = \frac{1}{2}(\overline{x}_1 + \overline{x}_2) + \lambda \begin{pmatrix} 0 & -1 \\ 1 & 0 \end{pmatrix}(\overline{x}_1 - \overline{x}_2) \quad (7)$$

$$r(\lambda) = |\overline{x}_1 - \overline{m}(\lambda)|$$

2. Calculate the distances to the other two points:

$$d_3(\lambda) = |\overline{m}(\lambda) - \overline{x}_3| - |r(\lambda) + d_{prox}|$$

$$d_4(\lambda) = |\overline{m}(\lambda) - \overline{x}_4| - |r(\lambda) + d_{dist}| \quad (8)$$

3. Find the midpoint $\overline{m}(\lambda)$ and inner radius $r(\lambda)$ by minimizing $d_3(\lambda)^2 + d_4(\lambda)^2$ to $\lambda$ The reference diameter within the "Pentagon of Confluence" is determined by using the Diameter measurement method as describe before.

The tubular organs may comprise an artery, a vein, a coronary artery, a carotid artery, a pulmonary artery, a renal artery, a hepatic artery, a femoral artery, a mesenteric artery or other tubular organ acquired from angiographic imaging. This allows a broad field for applying the invention.

Often, the polygon is a Pentagon of Confluence with vertices at either edge of said tubular organs, and a shared vertex among two distal said tubular organs. This is in fact quite a common situation, which lends itself to straightforward analysis.

A straightforward and fast procedure has the bifurcation identified through beginning at a start point in a proximal tubular organ (50) up to end points (31, 39) in respective distal tubular organs (52, 54). In particular, the diameter values are determined along the bifurcation.

Advantageously, a new metric is defined through determining a bifurcation diameter within the pentagon of confluence as extending between two artery edge points (72-74) that are closest to a single bifurcation center line point (70 in FIG. 9).

Advantageously, the angle between proximal and distal arteries is determined from lines extending between points on the centerlines outside the Polygon of Confluence (50, 52, 54, 60, 64, 66). This is a fast procedure.

Advantageously, the input for identifying a bifurcation is a single point (36) approximating a centre of the bifurcation.

Advantageously, a procedure is used as being enabled by a single start point for tracing a single tubular organ segment between a proximal and a distal bifurcation until a bifurcation is met or until a predetermined distance has been covered. The method may well be applied for detecting a multiple vessel tree bifurcation combination.

Advantageously, a reference bifurcation is modeled by a set of annuli with an inner circular edge fitted to an inner artery edge curve and an outer circular edge being fitted to an opposite artery edge curve (FIGS. 11a, 11b).

Now, the invention has been described by means of preferred embodiments. However, persons skilled in the art will readily recognize various amendments and variations thereto. In consequence, the disclosure should be considered as illustrative instead of limiting, and no limitations should be construed otherwise than such that are explicitly recited by the appended claims.

What is claimed is:

1. A method for executing quantitative analysis on medical image data depicting lengthwise extent of a bifurcated tubular organ comprising at least a proximal part, a first distal part and a second distal part, the method comprising:

(a) processing said medical image data to identify contours of said bifurcated tubular organ along its lengthwise extent, said contours including first and second outer contours and a middle contour therebetween;

(b) using said contours identified in (a) to determine a closed plane figure spanning lengthwise extent of said bifurcated tubular organ, wherein said closed plane figure is bounded by a plurality of lines meeting at vertices, the plurality of lines identifying a proximal start of said proximal part of said bifurcated tubular organ as well as distal ends of said first and second distal parts of said bifurcated tubular organ, wherein a first line of said plurality of lines lies along and follows the first outer contour as identified in (a), and wherein a second line of said plurality of lines lies along and follows the second outer contour as identified in (a);

(c) using said closed plane figure to determine at least one parameter value characterizing geometry of said bifurcated tubular organ; and (d) outputting said at least one parameter value to a user.

2. A method according to claim 1, wherein:
the at least one parameter value comprises at least one diameter value of said bifurcated tubular organ.

3. A method according to claim 2, wherein:
the at least one diameter value is selected from the group including a diameter value of the proximal part of the bifurcated tubular organ, a diameter value of the first distal part of the bifurcated tubular organ, and a diameter value of the second distal part of the bifurcated tubular organ.

4. A method according to claim 2, wherein:
the at least one diameter value is derived from a distance between two points on the lines of the closed plane figure.

5. A method according to claim 4, wherein:
said two border points are identified by scanning points on the lines of the closed plane figure to identify those two points that are closest to a centerline point within the closed plane figure.

6. A method according to claim 1, wherein:
the at least one parameter value comprises at least one angle value between parts of said bifurcated tubular organ.

7. A method according to claim 6, wherein:
the at least one angle is selected from the group including an angle between the proximal and first distal parts of the bifurcated tubular organ, an angle between the proximal and second distal parts of the bifurcated tubular organ, and an angle between the first and second distal parts of the bifurcated tubular organ.

8. A method according to claim 7, wherein:
the at least one angle is derived from a line extending between a centerline point on a line of the closed plane figure and a centerline point outside the closed plane figure.

9. A method according to claim 1, wherein:
the at least one parameter comprises at least one reference diameter value for said bifurcated tubular organ, the at least one reference diameter value compensating for damage to the bifurcated tubular organ.

10. A method according to claim 9, wherein:
the at least one reference diameter value is selected from the group including a reference diameter value for the proximal part of the bifurcated tubular organ, a reference diameter value of the first distal part of the bifurcated tubular organ, and a reference diameter value of the second distal part of the bifurcated tubular organ.

11. A method according to claim 9, wherein:
the at least one reference diameter value is derived from a set of annuli with an inner circular edge fitted to an inner edge curve and an outer circular edge fitted to an opposite edge curve.

12. A method according to claim 1, wherein:
said lines of said closed plane figure are derived from a point which lies at the center of a circle that fits inside said bifurcated tubular organ.

13. A method according to claim 12, wherein:
said lines of said closed plane figure are derived from line pieces passing through an intersection point between said circle and centerlines of said proximal part, said first distal part and said second distal part, respectively.

14. A method according to claim 1, wherein:
said closed plane figure has five vertices including a vertex adjacent intersection of the first and second distal parts of the bifurcated tubular organ.

15. A method according to claim 1, wherein:
the contours of the bifurcated tubular organ are derived from user identification of a single point that approximates a center of bifurcation of the bifurcated tubular organ.

16. A method according to claim 1, wherein:
the contours of the bifurcated tubular organ are derived from a single-point trigger for following a single tubular organ segment starting at a detected proximal bifurcation or at a predefined distance from the initial point, whichever is closer to the initial point, and ending at a detected distal bifurcation or at a predetermined distance from the initial point, whichever is first.

17. A method according to claim 1, wherein:
the method is adapted to affect multiple bifurcation analysis for detecting a multiple-vessel-tree bifurcation combination.

18. A method according to claim 1, wherein:
the bifurcated tubular organ is selected from the group including an artery, a vein, a coronary artery, a carotid artery, a pulmonary artery, a renal artery, a hepatic artery, a femoral artery, and a mesenteric artery.

19. A method according to claim 1, wherein:
the first and second lines that lie along respective contours of said bifurcated tubular organ are curved in the event that the respective contour is curved.

20. A data processing facility for quantitative analysis of medical image data depicting lengthwise extent of a bifurcated tubular organ comprising at least a proximal part, a first distal part and a second distal part, the data processing facility comprising:

first means for processing said medical image data to identify contours of said bifurcated tubular organ along its lengthwise extent, said contours including first and second outer contours and a middle contour therebetween;

second means for determining a closed plane figure spanning lengthwise extent of said bifurcated tubular organ based upon said contours identified by said first means, wherein said closed plane figure is bounded by a plurality of lines meeting at vertices, the plurality of lines identifying a proximal start of said proximal part of said bifurcated tubular organ as well as distal ends of said first and second distal parts of said bifurcated tubular organ, wherein a first line of said plurality of lines lies along and follows the first outer contour as identified by said first means, and wherein a second line of said plurality of lines lies along the second outer contour as identified by said first means;

third means for determining at least one parameter value characterizing geometry of said bifurcated tubular organ based upon said closed plane figure; and fourth means for outputting said at least one parameter value to a user.

21. A data processing facility according to claim 20, wherein:

the at least one parameter value is selected from the group including at least one diameter value of said bifurcated tubular organ, at least one angle value between parts of said bifurcated tubular organ, and at least one reference diameter value for said bifurcated tubular organ, the at least one reference diameter value compensating for damage to the bifurcated tubular organ.

22. A data processing facility according to claim 20, wherein:

the first and second lines that lie along respective contours of said bifurcated tubular organ are curved in the event that the respective contour is curved.

23. A non-transitory computer readable medium, tangibly embodying a program of instructions executable by a computer to perform method steps for quantitative analysis of medical image data depicting lengthwise extent of a bifurcated tubular organ comprising at least a proximal part, a first distal part and a second distal part, said method steps comprising:

(a) processing said medical image data to identify contours of said bifurcated tubular organ along its lengthwise extent, said contours including first and second outer contours and a middle contour therebetween;

(b) using said contours identified in (a) to determine a closed plane figure spanning lengthwise extent of said bifurcated tubular organ, wherein said closed plane figure is bounded by a plurality of lines meeting at vertices, the plurality of lines identifying a proximal start of said proximal part of said bifurcated tubular organ as well as distal ends of said first and second distal parts of said bifurcated tubular organ, wherein a first line of said plurality of lines lies along and follows the first outer contour as identified in (a), and wherein a second line of said plurality of lines lies along and follows the second outer contour as identified in (a);

(c) using said closed plane figure to determine at least one parameter value characterizing geometry of said bifurcated tubular organ; and (d) outputting said at least one parameter value to a user.

24. A non-transitory computer readable medium according to claim 23, wherein:

the at least one parameter value is selected from the group including at least one diameter value of said bifurcated tubular organ, at least one angle value between parts of said bifurcated tubular organ, and at least one reference diameter value for said bifurcated tubular organ, the at least one reference diameter value compensating for damage to the bifurcated tubular organ.

25. A non-transitory computer readable medium according to claim 23, wherein:

the first and second lines that lie along and follow respective contours of said bifurcated tubular organ are curved in the event that the respective contour is curved.

* * * * *